United States Patent [19]

Iscovich

[11] Patent Number: 5,395,343
[45] Date of Patent: Mar. 7, 1995

[54] ANCHORING DEVICE FOR MEDICAL TUBING

[76] Inventor: Angel Iscovich, 642 Via Trepadora, Santa Barbara, Calif. 93110

[21] Appl. No.: 139,947

[22] Filed: Oct. 21, 1993

[51] Int. Cl.6 .............................................. A61M 5/32
[52] U.S. Cl. .......................... 604/179; 128/DIG. 26; 24/16 PB; 604/174
[58] Field of Search ................ 604/174, 177, 178–180; 128/DIG. 6, DIG. 26; 24/16 PB, 17 AP, 30.5 R, 16 R, 17 A, 17 B, 19, 270, 271, 30.5 W, 31 R, 30.5 P, 35, 30.55, 30.5 L, 68 E, 68 F, 464, 465, 470, 472, DIG. 16; 248/74.2, 74.3

[56] References Cited

U.S. PATENT DOCUMENTS

| | | | |
|---|---|---|---|
| 3,059,645 | 10/1962 | Hasbrouck et al. | 604/179 |
| 3,224,056 | 12/1965 | Joffe | 24/16 PB |
| 3,257,694 | 6/1966 | Litwin | 24/16 PB |
| 3,568,262 | 3/1971 | Woldman | 24/16 PB |
| 3,739,429 | 6/1973 | Kohke | 24/16 PB |
| 4,263,697 | 4/1981 | Speedie | 24/30.5 L |
| 4,392,857 | 7/1983 | Beran | 604/179 |
| 4,466,160 | 8/1984 | de Lima Castro Netto | 24/30.5 R |
| 4,788,751 | 12/1988 | Shely et al. | 24/16 PB |
| 4,874,380 | 10/1989 | Hesketh | 604/180 |
| 4,910,831 | 3/1990 | Bingold | 24/16 PB |
| 5,031,943 | 7/1991 | Scott et al. | 24/16 PB |
| 5,088,158 | 2/1992 | Burkholder | 24/16 PB |
| 5,123,686 | 6/1992 | Wenk | 24/16 PB |
| 5,146,654 | 9/1992 | Caveney et al. | 24/16 PB |
| 5,193,254 | 3/1993 | Geisinger | 24/16 PB |
| 5,224,244 | 7/1993 | Ikeda et al. | 24/16 PB |

FOREIGN PATENT DOCUMENTS 2219034 11/1989 United Kingdom ................ 604/174

Primary Examiner—C. Fred Rosenbaum
Assistant Examiner—Ronald K. Stright, Jr.
Attorney, Agent, or Firm—Michael G. Petit

[57] ABSTRACT

A tube securing device is described which is useful for fixing the position of a medical tubing, such as a thoracostomy tube, with respect to the skin of a patient. The anchoring device comprises a unitary strap resembling a cable tie having a free end, a body portion and a buckle end. The buckle end has two or more unidirectional locking mechanism thereon for enabling movement of the body portion of the strap in only one direction. In operation, the body portion of the device is wrapped around the invasive medical tubing at the point where it enters the skin and the free end of the strap is passed through the first unidirectional locking mechanism on the buckle portion to form a first loop which encircles and grasps the tubing. The loop may be taped to the body to secure the tubing in position. A special release loop is provided that enables removal of the anchoring device from the tubing without damaging the tubing. In another embodiment, the free end of the anchoring device is passed around the tubing and passed through the first locking mechanism in the buckle portion once as described above and then through a second locking mechanism in the buckle portion a second time to make a second loop which may be taped to the skin to secure the device in position. In yet another embodiment the free end may be passed through the first locking mechanism to encircle the tube, then through the second locking mechanism to form a second loop as before, then through a third locking mechanism to form a third loop. The second and third loops form a "Figure 8" or "bow tie" back into the buckle a third time, forming a bow tie. The two loops of the bow tie may then be taped down securely to the skin. The device obviates the need for tape applied to the tubing.

1 Claim, 2 Drawing Sheets

ANCHORING DEVICE FOR MEDICAL TUBING

BACKGROUND OF THE INVENTION

1. Field of the Invention

This invention relates to a tube securing device for affixing medical tubing to the skin of a patient and, more particularly to a device for securing a thoracostomy tube to the skin of a patient.

2. Description of Prior Art

During the placement of larger medical tubes such as thoracostomy tubes, endotracheal tubes, and nasogastric tubes, it is important to secure the tube in position. It is particularly important that the tube remain stable and without movement in the longitudinal direction. Currently, these tubes are most commonly secured by wrapping tape around the tube and taping to the skin, or by suturing the tubing to the patient's skin. The difficulty occurs when wrapping tape or suture materials around a smooth tube. When a wet tubing is pulled on, the tape and suture material can slip or come undone allowing movement of the tubing and the resulting inability to secure the tube. Furthermore, it is cumbersome to remove tape or suture material from the tube when repositioning the tube without moving in a longitudinal direction.

Many devices have been described for securing endotracheal tubes and nasogastric tubes in position with respect to some external reference point on the skin of a patient. Representative of such tube holders are U.S. Pat. Nos. 4,449,527; 5,060,645; 5,069,206; and European Patent EP356683 A. Such devices use complex locking mechanisms and often rely on tape or sutures to secure the tubing to the device. Moreover, these devices frequently include several parts and are, therefore, not unitary. They are often bulky and include a significant area of the device which lies on the face or mouth for stabilization. Such devices often provide reduction in horizontal movement at the expense of ease in placement. While such tube holders may be preferable in endotracheal tubes, which are utilized in a long term chronic setting, no simple device, unitary is currently available for securing a thoracostomy tube to the patient's body. The convention is to use a suture tie material attached to the skin incision around the tube to secure it. No device is currently available that can attach to the suture tie material and thereby secure the tubing.

The foregoing limitations in prior art tube holders with respect to securing or anchoring a thoracostomy tube in position so as to prevent vertical or longitudinal motion suggests a different approach to holder design is appropriate. What is truly required is a unitary device which can be made inexpensively and can be placed quickly around a thoracostomy tube in either an emergency or elective setting. Further, it would also be desirable if such a tube holding device provided means for facile removal from the tubing without injuring or moving the tubing.

SUMMARY OF THE INVENTION

The general object of this invention is to provide an anchoring device for a thoracostomy tube which may be easily placed in position to anchor the tube.

It is an object of this invention to provide an anchoring device for an invasive medical tubing which does not require wrapping tape or other adhesive around the tubing in order to secure it to the patient's body.

It is another object of this invention to provide an anchoring device which is of unitary construction.

It is still another object of this invention to provide an anchoring device which may be easily released from its encircling position around medical tubing with a pair of scissors or other cutting implement without damaging the tubing.

These and other objects of the invention will soon become apparent as we turn now to drawings and a brief description of the preferred embodiments.

DESCRIPTION OF THE PREFERRED EMBODIMENTS

Figure 1:
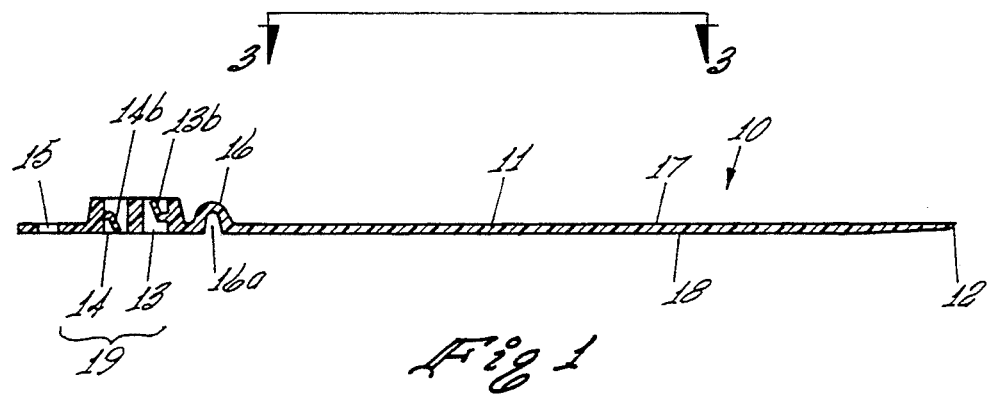
FIG. 1 is a side view of the anchoring device of the present invention.

Turning first to FIG. 1, a double buckle embodiment of the present invention is shown in side view. The anchoring device 10 comprises a single unitary piece having; a free end 12, an elongate body portion 11 and a buckle portion 19. The buckle portion 19 has a suture loop 15 projecting from the end of the buckle portion in a direction opposite to the free end of the device. The body portion 11 has an outer surface 17 and an inner surface 18. Adjacent to the buckle portion 19 is a safety loop 16. The safety loop 16 comprises a portion of the body portion 11 with a loop therein providing a slot 16a into which a scissors may be inserted. The safety loop 16 enables the health care worker to easily cut the device 10 free from a tubing by means of inserting a cutting implement into the slot 16a of the safety loop 16. The buckle portion 19 has at least two unidirectional locking means therein; a first locking means 13 and a second locking means 14. First locking means 13 and second locking means 14 are slots 13a and 14a with flexible tongues 13b and 14b projecting thereinto.

Figure 2:
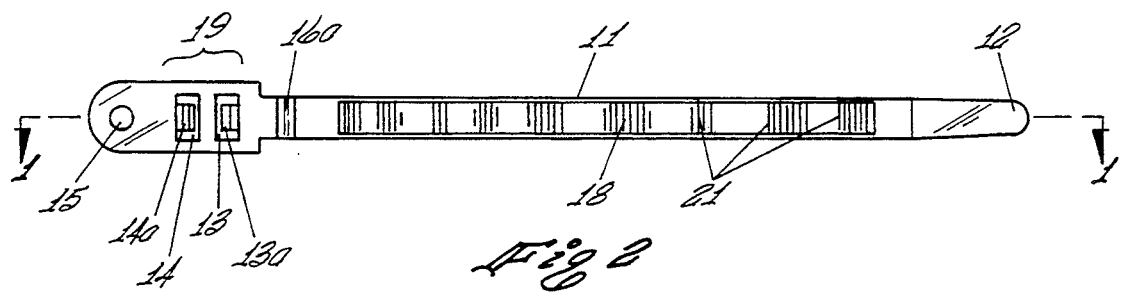
FIG. 2 a bottom view of the anchoring device of FIG. 1.

The anchoring device 10 of the present invention is shown in bottom view in FIG. 2, wherein the device 10 has a pattern of grooves 21 embossed or molded into the inner surface 18 of the body portion 11 of the device 10. The grooves 21 are dimensioned so that when the free end 12 of the device 10 is passed through the first locking means 13, the tongue 13b within the locking means 13 lockingly engages the groove so that the free end 12 cannot be pulled back out of the first locking means 13.

Figure 3:
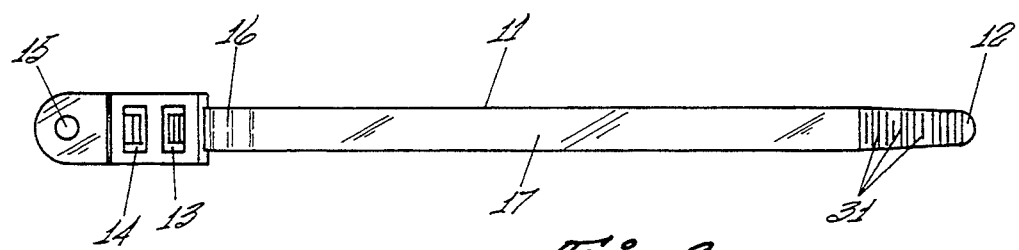
FIG. 3 is a top view of the anchoring device of FIG. 1.

The top view of the anchoring device of the present invention is shown in FIG. 3 wherein the body portion 11 has an outer side 17 which has a second set of grooves 31 located near the free end 12 of the device 10. The dimensions and spacing of the grooves 31 are such that when the free end 12 of the locking device 10 is passed through the second locking means 14, the free end 12 may be readily advanced. The free end 12 may no be pulled back out of the second locking means because the flexible tongue 14b projecting into the second locking means 14 lockingly engages the grooves 31, preventing the retreat of free end 12 from being removed from the second locking means 14.

Figure 4:
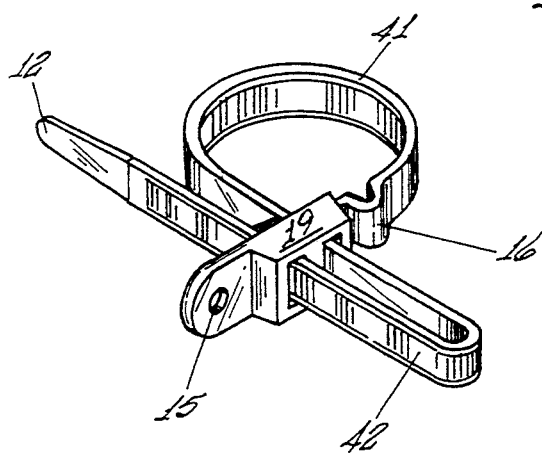
FIG. 4 is a perspective view of the anchoring device of FIGS. 1–3 in position for securing an invasive medical tubing.

FIG. 4 shows the locking device 10 of the present device in a configuration useful for securing a tube to a patient. A first loop 41 is created by passing the free end 12 through the first locking means 13 and pulling it through so that it forms loop 41. The free end is then doubled back and brought through second locking means 14 to create a second loop 42. Loop 41 encircles the tubing (not shown) whereas loop 42 is useful for taping the device 10 to the skin (not shown).

Figure 5:
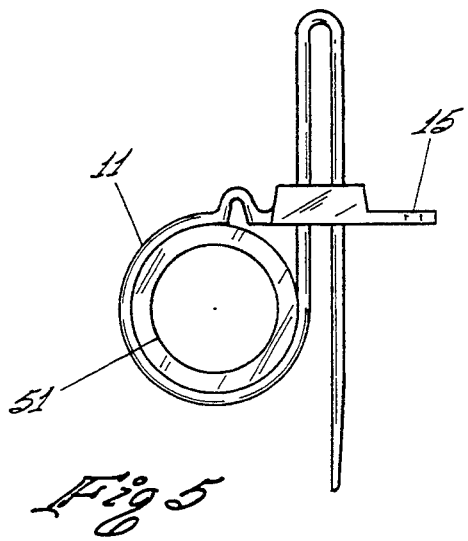
FIG. 5 is a top view of the anchoring device of FIGS. 1–4 securing a medical tubing in position.

FIG. 5 is a top view of the device 10 encircling a tube 51. The first loop 41 encircles the tube 51 and free end 12 is passed through the first locking means 13 to create a second loop 42. The second loop 42 can then be used to tape the device to the skin.

Figure 6:
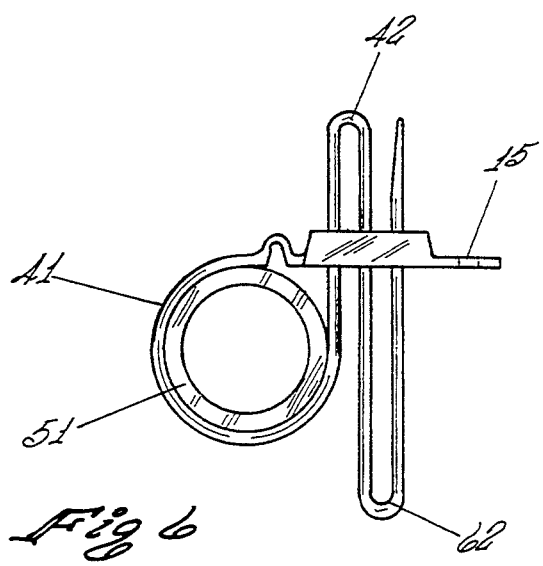
FIG. 6 is another top view of the anchoring device wherein a double bow confirmation is desired to secure the anchoring device to the skin.

FIG. 6 is a top view of another preferred embodiment of the device which is the same as that shown in FIG. 5 except that a third locking means 61 has been added to the buckle portion 19. Third locking means 61 is used to make yet another loop 62 to form a "Figure 8". Loops 42 and 62 may be taped to the skin (not shown) to secure the tube 51 in position.

Figure 7:
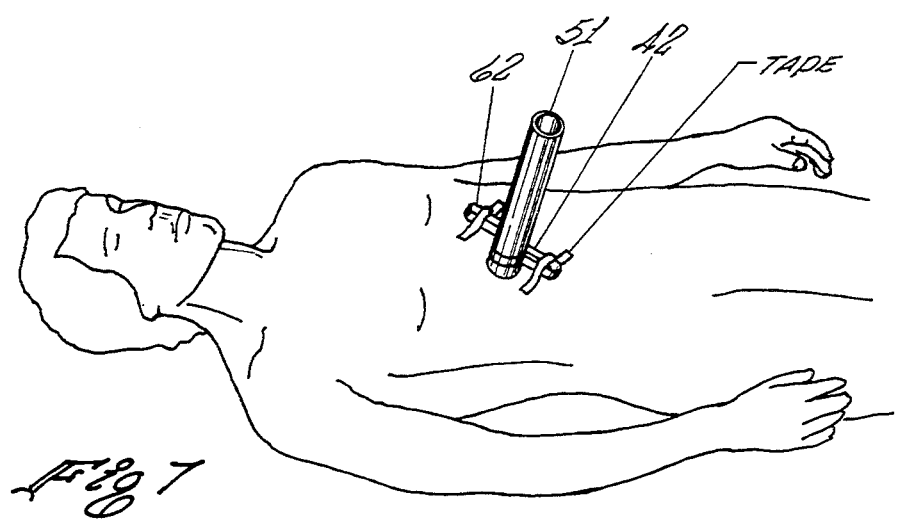
FIG. 7 shows a schematic view of the anchoring device of the present invention used to secure a thoracostomy tube to the skin of a patient.

FIG. 7 shows a patient 71 with a thoracostomy tube 51 entering the chest. The thoracostomy tube 51 is encircled by the body portion of the device 10. Which, after being looped through the locking means in the buckle portion 19 is taped to the chest thereby anchoring the tube to the skin.

Figure 8:
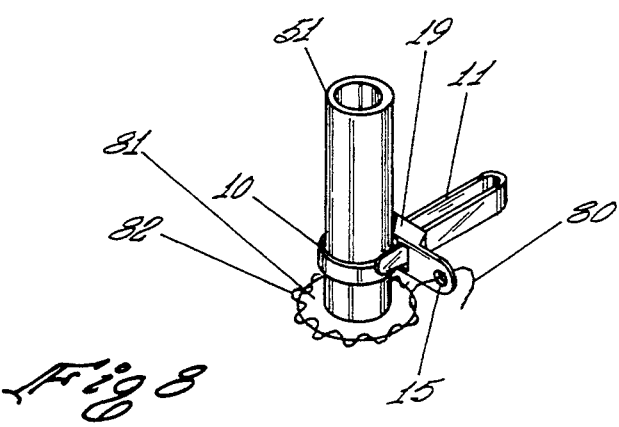
FIG. 8 shows the stitch loop of the present invention being used to secure the anchoring device to the skin by means of purse string suture around the thoracostomy tube.

FIG. 8 shows a thoracostomy tube 51 entering a wound 81 that has a purse string suture 82 surrounding the wound. The anchoring device 10 has a suture loop 15 distal to the buckle portion 19 which permits the attachment of the purse string suture to the anchoring device 10, thereby securing it to the skin.

When the tube 51 has been placed in the desired position and is ready to be secured, the device 10 is wrapped around the tube adjacent to its entry into the body cavity (anywhere from ¼" to 1" from entry, depending upon type of tube). The body portion 11 encircles the tubing 51 and the free end 12 is placed through the first locking means and cinched firmly to the tube. The tube 51 is slightly compressed uniformly and the device 10 is securely affixed thereto. One may test to be certain that the device 10 does not move with respect to the tubing 51 by pulling on the free end 12 to ascertain if movement is possible. If the device is loose, cinch the device tighter without collapsing the tube. If the tube 51 is a thoracostomy tube, the suture needle 80 (from the incision site 81 where the purse string suture 82 is placed) should be wrapped several times around the tube 51 proximal to the device 10 and put through the suture attachment hole 15 and tied and cut. The remainder of the body portion may be used to make second and/or third loops via the second locking means and/or third locking means or simply cut off. The second loop which is developed after threading the free end through the second locking means is used to secure tape to the device and subsequently to the patient's skin. This second loop can be cinched tightly once the tape is securely fastened and applied to the patient's skin. The remainder of the body portion and free end may be cut off or used to create a third loop. The second loop is for securing tubes to patients with tape (i.e.: nasotracheal tube, endotracheal tube, nasogastric tube, or a gastric tube, etc.). After the anchoring device is in place, if it is necessary to adjust the tube, the device can simply be removed by cutting it off at the safety loop. Thus, not only can the device be quickly released from the tubing, it will not damage the tube because the cutting implement does not have to be slid between the tube contacting portion and the device. A slot is provided for insertion of a cutting tool. The safety loop provides a safe way of removing the anchoring device from its encircling position around the tube without damaging the tube. The second loop formed by taking the free end of the anchoring device and passing it through the second locking means to form a second loop, is useful not only for taping the anchoring device to the skin, but for hanging the device up on a hook or the like should it be so desired.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A device for securing a medical tubing to the skin of a patient comprising a unitary elongate member having a buckle portion, a free end, and a body portion therebetween dimensioned to at least encircle the medical tubing, and wherein said buckle portion has at least first and second unidirectional locking means thereon which first and second locking means engage groove means on said body portion of said device when said free end is passed through said first and second locking means in only one direction, and wherein said body portion is of uniform thickness and has at least one loop therein, said loop creating a semicircular space between the semicircular portion of said body portion needed and the medical tubing when said body portion is in an encircling position around the medical tubing and wherein said space is dimensioned to accept at least a portion of a cutting tool therewithin.

* * * * *